US00PP21781P2

(12) United States Plant Patent
Hurd

(10) Patent No.: US PP21,781 P2
(45) Date of Patent: Mar. 15, 2011

(54) ***DIANTHUS* PLANT NAMED 'SANGRIA SPLASH'**

(50) Latin Name: ***Dianthus* hybrid**
Varietal Denomination: Sangria Splash

(75) Inventor: Kevin Hurd, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 12/462,741

(22) Filed: Aug. 7, 2009

(51) Int. Cl.
*A01H 5/00* (2006.01)

(52) U.S. Cl. ..... Plt./272
(58) Field of Classification Search ..... Plt./272

See application file for complete search history.

*Primary Examiner*—Susan B McCormick Ewoldt

(57) ABSTRACT

The new and distinct cultivar of perennial Carnation or Pinks, *Dianthus* plant named 'Sangria Splash' with long-blooming, fragrant, single flowers, with petals that begin deep red with fuchsia spots and then becomes lighter in both the center petal portion and the margin portion. *Dianthus* 'Sangria Splash' is tolerant of high temperatures and resists center die-out.

2 Drawing Sheets

Botanical denomination: *Dianthus* hybrid.

Cultivar designation: 'Sangria Splash'.

BACKGROUND OF THE INVENTION

The present invention relates to the new and distinct cultivar of *Dianthus* or Pinks from the genus *Dianthus* and given the cultivar name 'Sangria Splash'. The new plant was the result of an intentional cross in May of 2006 by Kevin A. Hurd between *Dianthuis gratianopolitanus* 'Feuerhexe' also known as 'Firewitch', (not patented) as the seed parent and 'Devon Siskin' U.S. Plant Pat. No. 14,377 (more often known as 'Raspberry Swirl') as the pollen parent. The new hybrid was first isolated from trials at a nursery in Zeeland, Mich. during the summer of 2007. *Dianthus* 'Sangria Splash' has been asexually propagated at the same nursery in Zeeland, Mich. using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Flat, single, overlapping petals of fuchsia pink with crimson and pink.
2. Unique floral color pattern.
3. High heat tolerance.
4. Floriferous habit.
5. Vigorous growth and excellent habit.
6. Compact, fine-textured, blue-green foliage.

Cultivar Comparison Table

| Cultivar | Flower color | Flower pattern | Flower size | Petal margin | Petal # | Plant height in flower |
|---|---|---|---|---|---|---|
| 'Apple Slice' application No. 12/462,743 | pink | dark wine edge and rim | 4.5 cm | dark wine margin | 20 to 24 | 22 cm |
| 'Black Cherry Wild' application No. 12/462,742 | burgundy | solid | 4.0 cm | light rose margin | 16 to 20 | 22 cm |
| 'Coconut Punch' application No. 12/462,744 | white | burgundy edge with white rim | 3.5 cm | reddish purple margin | 14 to 30 | 28 cm |
| 'Double Spotty' U.S. Plant Pat. No. 13,884 | burgundy | white picotee edge and white spots | 4.0 cm | white | 15 to 20 | 17 to 30 cm |
| 'Dragon Fruit' application No. 12/462,745 | fuchsia pink | red jagged purple bar | 3.5 cm | self | 14 to 22 | 20 cm |
| 'Pomegranate Kiss' application No. 12/462,746 | burgundy | irregular pink splashing on margin or center | 3.2 cm | irregular pink splashing | 16 to 22 | 16 cm |
| 'Cranberry Ice' U.S. Plant Pat. No. 18,342 | pink | dark wine edge and rim | 3.3 cm | dark wine margin | 5 | 20 to 25 cm |
| 'Devon Siskin' U.S. Plant Pat. No. 14,377 | light pink | magenta edge with burgundy base | 4.0 cm | magenta edge | 5 | 10 cm |
| 'Feuerhexe' (not patented) | pink | solid | 4.0 cm | self | 5 | 10 to 12 cm |
| 'Devon Xera' U.S. Plant Pat. No.14,895 | red | crimson eye | 3.0 cm | self | 5 | 15 to 20 cm |
| Red Dwarf' U.S. Plant Pat. No. 14,437 | red | crimson eye | 3.5 cm | self | 5 | 20 to 25 cm |

-continued

Cultivar Comparison Table

| Cultivar | Flower color | Flower pattern | Flower size | Petal margin | Petal # | Plant height in flower |
|---|---|---|---|---|---|---|
| 'Sangria Splash' application No. 12/462,741 | fuchsia pink | crimson ring with pink splashing and center | 3.0 cm | crimson with pink splashing | 5 | 30 cm |
| 'Spangled Star' U.S. Plant Pat. No. 13,029 | scarlet red | small white spots and white picotee edge | 4.0 cm | white picotee edge | 5 | 17 to 22 cm |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
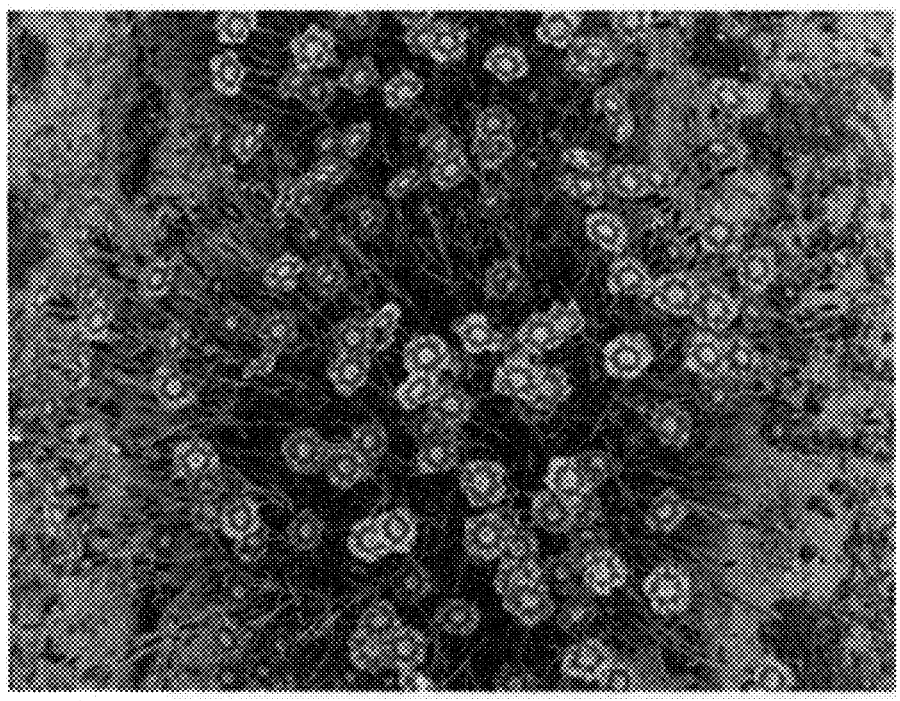
FIG. 1 shows the new plant at two-years of age in flower.
Figure 2:
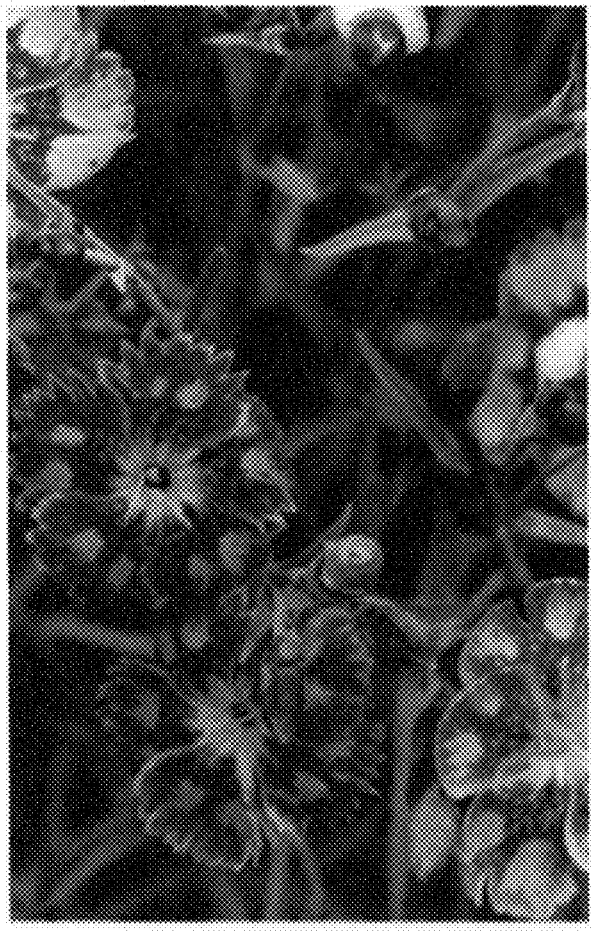
FIG. 2 shows a close-up of the flower and bud.
Figure 3:
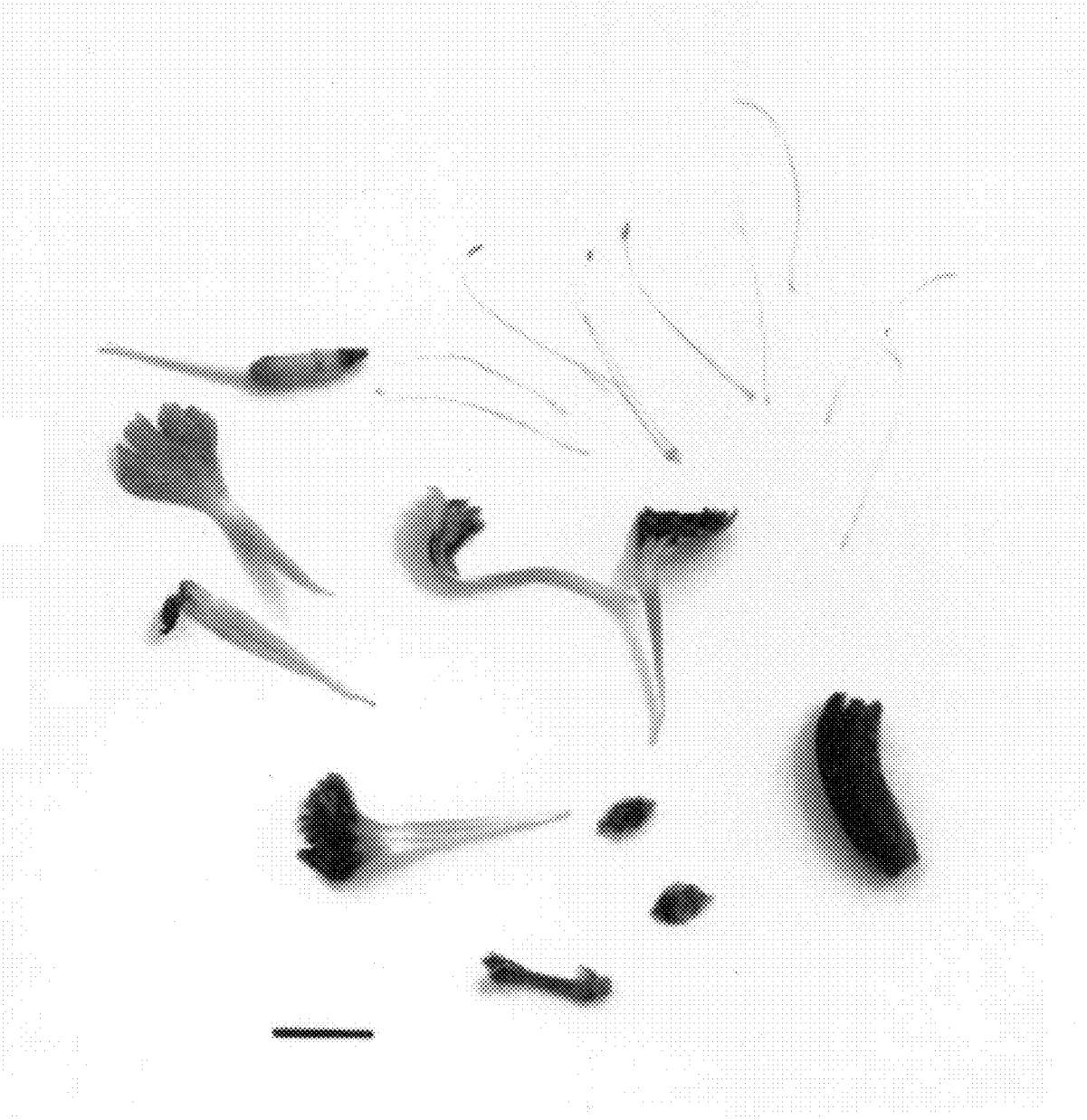
FIG. 3 shows the dissected flower of the new plant together with capsule and seeds.

The following detailed description of the new plant is based on observations of several two-year old plants in open-field, full-sun conditions in Zeeland, Mich. with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid.

Parentage: 'Feuerhexe' (female) times 'Raspberry Swirl' male parent.

Plant description:

*Habit.*—Cespitose, herbaceous, evergreen perennial; stems proximally branched, erect; height of foliage about 18 cm and 42 cm across; height in flower is about 30 cm; Root system; fibrous.

Foliage:

*Leaf type.*—Simple, linear, opposite, decussate, sessile, glabrous, glaucous on adaxial and abaxial; acute apex; base decurrent, adpressed along stem and somewhat perfoliate; no fragrance detected.

*Leaf dimensions.*—About 7.0 cm long and 2.0 mm wide.

*Leaf color.*—Nearest RHS 122B adaxial and abaxial sides.

*Venation.*—Finely reticulate, coloration same as that of leaf top and bottom.

*Stems.*—Erect to arching, terete, glabrous, glaucous, proximally branching at 2 to 3 nodes.

*Stem size.*—About 30 cm long and 2 mm wide at base.

*Stem color.*—Nearest RHS 122B.

*Branching.*—Numerous from lower leaf axils; about 200 per plant.

*Nodes.*—3 mm across, RHS N122C.

*Internodes.*—6.5 cm apart.

Inflorescence:

*Type.*—Terminal, cymose, erect, symmetrical.

*Dimension.*—About 2.5 cm across and extending about 7 mm above calyx.

*Flowers per stem.*—4 to 5.

*Pedicel.*—Glaucous, glabrous, terete.

*Pedicel size.*—Usually 2 cm long and 2 mm diameter.

*Pedicel color.*—Nearest RHS 122A.

Flowers:

*Type.*—Salviform, completely double, symmetrical.

*Dimension.*—About 3.0 cm across and extending about 1.3 cm above calyx.

*Flower bud shape.*—Rhomboid to terete.

*Flower bud size one day prior to opening.*—About 2.2 cm long and 0.5 cm wide.

*Flower bud color.*—Glaucous, between RHS N138C and RHS N138D, heavily pigmented with anthocyanin between RHS 187B and RHS N187B.

*Flower period.*—Beginning late May and flowering until frost in the fall with a short 2 week rest after the initial bust.

*Flower fragrance.*—Light, sweet spicy, clove-like.

*Flower lasting quality.*—About five days on or off the plant.

*Petals.*—5, consisting of a rounded blade or limb and a claw (enclosed completely within the calyx), obovate, apex dentate with dentations 1 mm deep, bearded with minute hairs mostly on the center of the adaxial surface, bent outwardly to nearly a ninety degree angle.

*Petal color.*—Petal limb base adaxial side between RHS N79B and RHS N79C with one or two irregular spots of RHS N74A; abaxial side limb nearest RHS N80C; adaxial slide of petal limb lightens to between RHS 73B and RHS 73C with base nearest RHS 64B; claw consistent RHS 145B on both sides with a 2 to 3 mm band of white lighter than RHS 150D on both adaxial and abaxial sides next to limb.

*Dimension.*—2.8 cm long including claw and limb; petal limb to 1.5 cm across and 1.4 cm long; claws 1.3 cm long and 2 mm to 4 mm wide about 3 mm from limb.

*Calyx.*—Glabrous, glaucous, five-toothed corolla tube fused in proximal 1.6 cm; about 2.0 cm long and 0.5 cm in diameter; between RHS N138C and RHS N138D, heavily pigmented with anthocyanin between RHS 187B and RHS N187B.

*Peduncle.*—Glabrous, glaucous, terete, 22 cm long and 2 mm diameter at base; RHS N138D.

*Bracts.*—Two, opposite, broadly obtuse with rounded apex, about 7 mm long and 7 mm wide; RHS 141A in the center, lighter than RHS 138D at base and margins.

*Bracteoles.*—Two, opposite, lanceolate, sharply acute apex, bases joined at stem; about 10 mm long and 2 mm wide; glaucous, RHS 141A at apex and center, lighter than RHS 138D at base and margins.

*Androecium.*—Stamens usually 10, filaments variable in length from 1.6 to 2.0 cm long, less than 1 mm diameter; pale green lighter than RHS 11D; anther oblong to 3.0 mm long and 1.0 mm wide, nearest RHS195C; pollen color RHS 11D.

*Gynoecium.*—Style split in two above ovary, pistil 1.6 cm long and about 1 mm diameter, lighter than RHS 11D except for distal 4 mm which are gradually darken to RHS 76C; stigma RHS 77C.

*Ovary.*—Superior, spindle-shaped; 8 mm long and 2.5 mm wide; RHS 145A at distal end and between RHS 145 D and RHS 145 C at proximal end.

Seed: 20 to 56, blackish brown darker than RHS 200A, shield-shaped, dorsiventrally compressed, about 3.0 mm across and 0.5 mm thick.

Capsule: Ovoid to cylindrical, opening by 4 teeth, about 2 cm long and 8.5 mm diameter, between RHS 197B and RHS 197 C.

Comparison varieties: The new plant is distinct from its parents and all other *dianthus* known to the inventor in that the new plant has single flowers unlike 'Double Spotty', has petals that begin deep red with fuchsia spots and then becomes lighter in both the center petal portion and the margin portion. The nearest comparison plant would be 'Cranberry Ice' U.S. Plant Pat. No. 18,342 which has similar base colored petals but without the rose pink splashing. The new plant also has deeper dentations in the petals than co-pending application Ser. No. 12/462,742 'Black Cherry Wild'.

Disease resistance: The new plant is resistance to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct cultivar of perennial Carnation or Pinks, *Dianthus* plant named 'Sangria Splash' as herein described and illustrated, with long-blooming, fragrant, single flowers, petals that begin deep red with fuchsia spots and then becomes lighter in both the center petal portion and the margin portion, tolerant of high temperatures, resists center die-out and suitable as a garden ornamental, potted plant and for cut flower arrangements.

* * * * *